US007514850B2

(12) United States Patent
Asai

(10) Patent No.: US 7,514,850 B2
(45) Date of Patent: Apr. 7, 2009

(54) POLYMER ACTUATOR

(75) Inventor: Katsuhiko Asai, Nara (JP)

(73) Assignee: Panasonic Corporation, Osaka (JP)

(*) Notice: Subject to any disclaimer, the term of this patent is extended or adjusted under 35 U.S.C. 154(b) by 158 days.

(21) Appl. No.: 11/790,748

(22) Filed: Apr. 27, 2007

(65) Prior Publication Data

US 2008/0169729 A1 Jul. 17, 2008

Related U.S. Application Data

(63) Continuation of application No. PCT/JP2006/314249, filed on Jul. 19, 2006.

(30) Foreign Application Priority Data

Aug. 23, 2005 (JP) ............................ 2005-240897

(51) Int. Cl.
*H01L 41/08* (2006.01)

(52) U.S. Cl. ..................................................... 310/328

(58) Field of Classification Search ................. 310/328, 310/323.02, 800
See application file for complete search history.

(56) References Cited

U.S. PATENT DOCUMENTS 6,847,155 B2 * 1/2005 Schwartz et al. ............ 310/328
7,233,097 B2 * 6/2007 Rosenthal et al. ........... 310/328
7,259,495 B2 * 8/2007 Asai et al. ................... 310/311
2004/0263028 A1 * 12/2004 Pei et al. ..................... 310/800
2007/0164641 A1 * 7/2007 Pelrine et al. ............... 310/800
2007/0200468 A1 * 8/2007 Heim ......................... 310/800
2007/0222344 A1 * 9/2007 Kornbluh et al. ............ 310/800

FOREIGN PATENT DOCUMENTS

JP 11-169393 6/1999
JP 2000-83389 3/2000
JP 2005-51949 2/2005
WO 2005/076452 8/2005

OTHER PUBLICATIONS

Patent Cooperation Treaty (PCT) International Preliminary Report on Patentability, issued on Feb. 26, 2008.

Ron Pelrine et al., "*High-Speed Electrically Actuated Elastomers With Strain Greater Than 100%*", Feb. 4, 2000, vol. 287, No. 5454, pp. 836-839.

Gordon G. Wallace et al., "*Factors Influencing Performance of Electrochemical Actuators Based on Inherently Conducting Polymers (ICPs)*", Smart Structures and Materials 2002: Electroactive Polymer Actuators and Devices, Proceedings of SPIE, vol. 4695, pp. 8-16.

* cited by examiner

*Primary Examiner*—Mark Budd
(74) *Attorney, Agent, or Firm*—Wenderoth, Lind & Ponack, L.L.P.

(57) ABSTRACT

In a polymer actuator driven by extension and contraction of the polymer by electrical stimulation, the displacement generated by extension and contraction of the polymer is taken out through a movable body connected to a second terminal member which is connected to one end of the polymer, by way of a first elastic body and pressed against a first terminal member which is connected to the other end of the polymer, by the elastic force of the first elastic body.

18 Claims, 11 Drawing Sheets

6
7
1
5a
2
10b
11a
+
-
8b
8a
4
10a
9b
9a
11b
5b

POLYMER ACTUATOR

This is a continuation application of International Application No. PCT/JP2006/314249, filed Jul. 19, 2006.

BACKGROUND OF THE INVENTION

The present invention relates to a polymer actuator that can suppress degradation even when forced displacement is externally applied, a robot arm driven by the polymer actuator, and a robot equipped with the robot arm.

With increase in demand for machines that operate near humans such as a household robot, expectations for an artificial muscle actuator that operates flexibly as in muscles of a human are also rising. Actuators of various types have been proposed as candidates for the artificial muscle actuator, among them are actuators using conductive polymers, actuators using dielectric polymers, and the like.

An actuator which generates flexural deformation as shown in FIGS. 5A, 5B, and 5C is proposed as one example of the artificial muscle actuator using a conductive polymer. The actuator has a configuration of sandwiching a solid electrolyte molding member 32 with polyaniline film members 35*a*, 35*b* serving as conductive polymer films. A potential difference set in a power supply 36 is applied between the polyaniline film members 35*a*, 35*b* by turning ON a switch 37, whereby negative ions enter one polyaniline film member 35*b* thereby extending the relevant film member and negative ions are released from the other polyaniline film member 35*a* thereby contracting the relevant film member as shown in FIG. 5B, and consequently, flexural deformation occurs (see e.g., patent document 1).

In such configuration, the flexural deformation occurs by the difference in displacement amount of the two conductive polymer film members 35*a*, 35*b* serving as electrodes, but an actuator is also known, which has a configuration where the electrolyte retention layer is formed by a liquid or gel substance to prevent deformations of both electrodes from influencing each other, and the displacement of only one of the conductive polymer film members 35*a*, 35*b* is taken out to conduct extending and contracting deformation. In this case, the electrode in which displacement is not used does not need to be a conductive polymer, and although metal electrodes are mainly used, it is shown that the displacement may be increased by arranging conductive polymers on the metal electrode (see e.g., non-patent document 1).

Such conductive polymer actuator produces distortion comparable to muscles at a low voltage of 2 to 3V, and thus is expected to be put to practical use as an artificial muscle.

An actuator that utilizes elastic deformation of polymers as shown in FIGS. 6A and 6B is proposed as one example of the artificial muscle actuator using dielectric polymers. The actuator is configured by a dielectric polymer 42 of a flat plate shape, flexible electrodes 41, 43 of a thin film shape made of carbon particles such as graphite or carbon black or metal arranged on both surfaces of the dielectric polymer 42, a power supply 46 connected between the electrodes 41, 43, and a switch 47. When the switch 47 is turned ON and the potential difference set in the power supply 46 is applied between the electrodes 41, 43, the dielectric polymer member 42 compresses, and expands in the lateral direction as shown in FIG. 6B. The dielectric polymer 42 restores to the state of FIG. 6A when the switch 47 is turned OFF.

Such an actuator produces a strain equal to or greater than 100% by using silicon rubber or acrylic for the dielectric polymer 42, and thus is expected to be put to practical use as the artificial muscle (see e.g., non-patent document 2).

However, in the case of the actuator using extending and contracting deformation of the polymers, a driving force in the extending direction cannot be produced as it is since the polymer is in a film shape, and thus must be used with the terminal members 55*a*, 55*b*, which are arranged at both ends of the polymer film 52, connected by elastic bodies 59*a*, 59*b* that generate elastic force in the extending direction, and with a preload applied in the extending direction, as shown in the configuration of FIG. 7.

Patent document 1: Japanese Unexamined Patent Publication No. 11-169393

Non-patent document 1: Proceedings of SPIE, Vol. 4695, pp. 8-16

Non-patent document 2: SCIENCE, Vol. 287, No. 5454, pp. 836-839

The actuators of the above-described configuration have a drawback in that the performance lowers when forced displacement is externally applied. For example, when forced displacement is applied in the contracting direction to the actuator configured by one polymer film 52 as shown in FIG. 8A, such displacement cannot be received by the polymer of a film shape, and the polymer film 52 tends to bend as in FIG. 8B. The reference characters in FIGS. 8A and 8B indicate the members denoted with the same reference characters in FIG. 7. The polymer film 52 is likely to bend particularly at the connecting part of the terminal members 55*a*, 55*b* and at the intermediate portion of the polymer film 52. When repeatedly subjected to displacement, effects such as lowering of the strength of the polymer film 52 at the bent region appear and the performance of the actuator lowers. In the case of a stacked polymer actuator as well, the load tends to be applied in the direction of stripping the electrode or the electrolyte retention layer from the polymer film, and thus the bond between each layer weakens and the actuation efficiency lowers.

If forced displacement is applied to the actuator in the extending direction, on the other hand, irreversible deformation occurs to the polymer film. Although the polymer film itself has elasticity of a certain degree, the film tends to be irreversibly deformed or restoration from the extended state is not possible, and in the worst case, may break if pulled at a load of greater than or equal to a certain level. If irreversible deformation occurs, the movable range of the polymer actuator offsets by such an amount, and the operation same as that before the occurrence of the irreversible deformation cannot be performed.

In order to respond to such situation, on the assumption that the actuator will degrade, methods such as allowing a margin of performance, arranging the elastic element in series with the actuator, arranging a stopper against the actuator displacement, and the like are proposed. However, allowing a margin of performance on the assumption that the actuator will degrade is not desirable in terms of efficiency. Furthermore, a flexible elastic element is required to suppress the force applied to the actuator by the forced displacement if arranging the elastic element in series with the actuator. In this case, however, the output generated by the actuator is also not transmitted to the outside, and thus it is not desirable. Moreover, if the stopper is used against the actuator displacement, the allowable deformation amount differs between slow extension by self-actuation or the like and fast forced displacement by external force since the polymer exhibits viscoelastic behavior, and thus protection of the polymer and performance of the actuator cannot be obtained simultaneously simply by arranging the stopper with respect to the displacement of the actuator where both slow extension and fast forced displacement appear in combination.

Accordingly, in view of the above aspects, an object of the present invention is to provide a polymer actuator that can suppress lowering of performance when forced displacement is externally applied to the actuator without suppressing the performance of the actuator, a robot arm driven by the polymer actuator, and a robot equipped with the robot arm.

SUMMARY OF THE INVENTION

The present invention proposes the following configurations to achieve the above aim.

According to a first aspect of the present invention, there is provided a polymer actuator being driven by extension and contraction of a polymer by electrical stimulation; the polymer actuator comprising:

a polymer film member configured by the polymer;

a first terminal member connected to one end of the polymer film member;

a second terminal member connected to the other end of the polymer film member; and a movable body connected to the second terminal member by way of a first elastic body and capable of being pressed against a first terminal member side; wherein a displacement generated by extension and contraction of the polymer film member is taken out by way of the movable body connected to the second terminal member which is connected to the other end of the polymer film member, by way of the first elastic body and pressed against the first terminal member which is connected to the one end of the polymer film member, by an elastic force of the first elastic body.

According to a 17th aspect of the present invention, there is provided a robot arm driven by the polymer actuator according to the first or second aspect.

According to an 18th aspect of the present invention, there is provided a robot comprising the robot arm according to the 17th aspect.

According to the present invention, the polymer actuator that can suppress degradation of the performance when forced displacement is externally applied to the actuator without suppressing the performance of the actuator is obtained. In other words, the displacement of the actuator is taken out through the movable body connected to the second terminal member on a fixed side, which is connected to the one end of the polymer, by way of the elastic body and pressed against the first terminal member on the movable side, which is connected to the other end of the polymer, by the elastic force of the elastic body, so that the movable body moves by the same extent in conjunction with the first terminal member unless the external force in the direction of from the first terminal member towards the second terminal member, that is, the external force displacing the actuator in the contracting direction, is applied to the actuator. Therefore, the output of the actuator becomes the same as that when directly taken out from the first terminal member. Furthermore, since the movable body can move in the direction of the second terminal member independent from the first terminal member when forced displacement is applied in the contracting direction of the actuator, the polymer will not bend and lowering of performance of the actuator can be suppressed.

BRIEF DESCRIPTION OF THE DRAWINGS

These and other aspects and features of the present invention will become clear from the following description taken in conjunction with the preferred embodiments thereof with reference to the accompanying drawings, in which.

DETAILED DESCRIPTION OF THE PREFERRED EMBODIMENTS

Figure 1A:
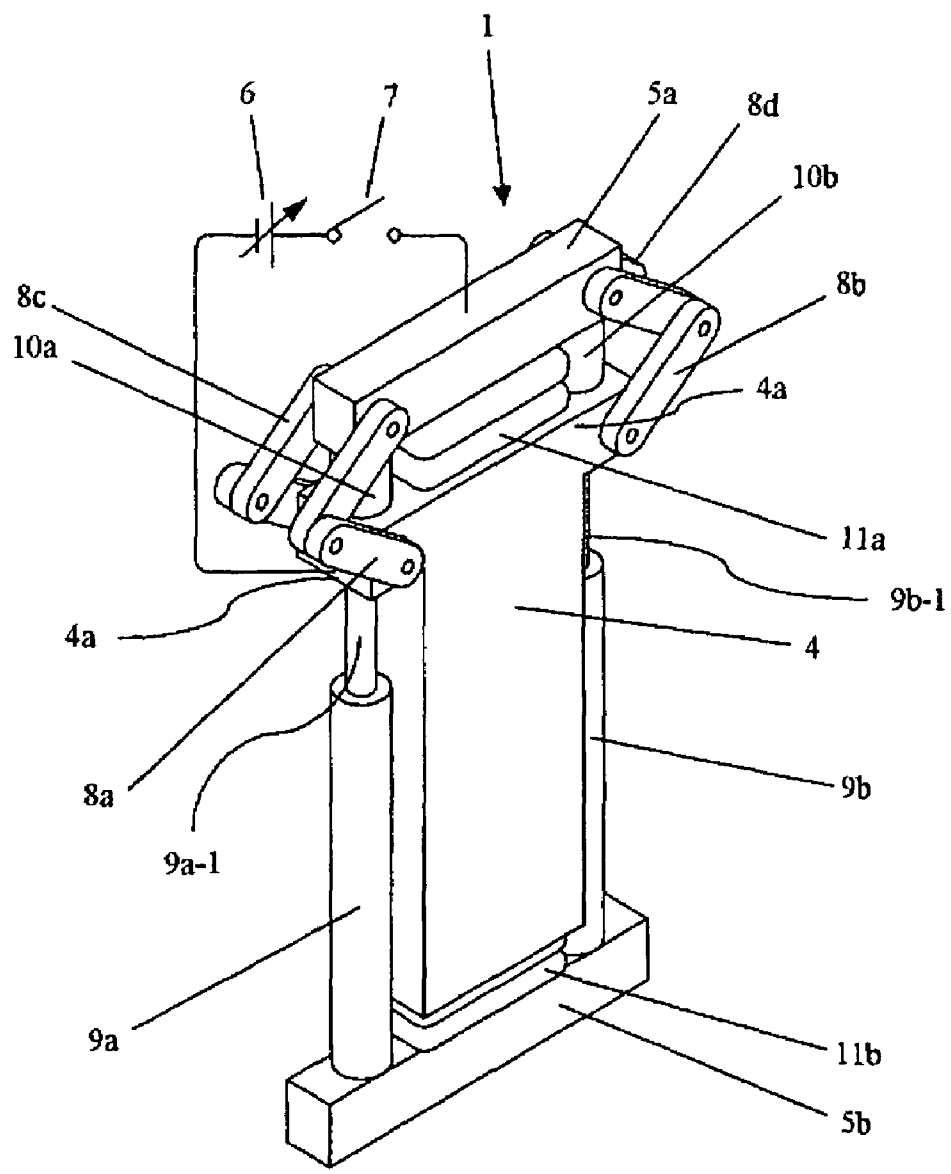
FIG. 1A is a schematic perspective view showing an artificial muscle actuator according to a first embodiment of the present invention.

Before the description of the present invention proceeds, it is to be noted that like parts are designated by like reference numerals throughout the accompanying drawings.

Prior to the detailed description of embodiments of the present invention based upon the drawings, various aspects for the present invention will be explained.

According to a first aspect of the present invention, there is provided a polymer actuator being driven by extension and contraction of a polymer by electrical stimulation; the polymer actuator comprising:

a polymer film member configured by the polymer;

a first terminal member connected to one end of the polymer film member;

a second terminal member connected to the other end of the polymer film member; and a movable body connected to the second terminal member by way of a first elastic body and capable of being pressed against a first terminal member side; wherein a displacement generated by extension and contraction of the polymer film member is taken out by way of the movable body connected to the second terminal member which is connected to the other end of the polymer film member, by way of the first elastic body and pressed against the first terminal member which is connected to the one end of the polymer film member, by an elastic force of the first elastic body.

According to such configuration, the movable body moves by the same extent in conjunction with the first terminal member unless the external force in the direction of from the first terminal member to the second terminal member, that is, the external force displacing the actuator in the contracting direction is applied to the actuator. Thus, the output of the actuator thus becomes the same as when directly taken out from the first terminal member. Furthermore, since the movable body can move in the direction of the second terminal member independent from the first terminal member when forced displacement is applied in the contracting direction of the actuator, the polymer will not bend and lowering of performance of the actuator can be suppressed. Therefore, the polymer actuator that suppresses lowering of performance when forced displacement is externally applied to the actuator is obtained.

According to a second aspect of the present invention, there is provided the polymer actuator according to the first aspect, wherein the polymer actuator includes two electrodes and the polymer film member of a dielectric polymer arranged therebetween, and is driven by extension and contraction generated at the dielectric polymer by applying a potential difference between the electrodes.

According to such configuration, the polymer actuator driven by extension and contraction of the dielectric polymer triggered by the electrical stimulation applied to the electrodes arranged on both sides of the polymer film member of the dielectric polymer can be obtained.

According to a third aspect of the present invention, there is provided the polymer actuator according to the first or second aspect, wherein the polymer actuator includes the polymer film member of the polymer having conductivity, and an electrode connected to the polymer having the conductivity by way of an electrolyte retention layer, and is driven by extension and contraction generated at the polymer having the conductivity by applying a potential difference between the polymer having the conductivity and the electrode.

According to such configuration, the polymer actuator can be obtained, which is driven by extension and contraction of the polymer film member of the polymer having conductivity triggered by the electrical stimulation applied between the polymer film member of the polymer having conductivity and the electrode connected thereto by way of the electrolyte retention layer.

According to a fourth aspect of the present invention, there is provided the polymer actuator according to the third aspect, wherein the movable body includes the polymer film member of the polymer having the conductivity and the electrode connected to the polymer film member by way of the electrolyte retention layer.

According to such configuration, the polymer actuator can be obtained in which a space used only for the movable body can be reduced, and the volume availability efficiency of the entire actuator can be enhanced since the electrode originally included in the actuator can be used as a constituting component of the movable body.

According to a fifth aspect of the present invention, there is provided the polymer actuator according to the third aspect, wherein the polymer having the conductivity is a polymer comprising an organic conductive polymer.

According to such configuration, the polymer actuator can be obtained, which is driven by extension and contraction of the organic conductive polymer involved in oxidation-reduction triggered by the electrical stimulation applied between the organic conductive polymer and the electrode connected thereto by way of the electrolyte retention layer.

According to a sixth aspect of the present invention, there is provided the polymer actuator according to the third aspect, wherein the polymer having the conductivity comprises a carbon material having conductivity.

According to such configuration, the polymer actuator can be obtained, which is driven by extension and contraction of the polymer structure triggered by the electrical stimulation applied between the polymer structure containing the carbon material having the conductivity and the electrode connected thereto by way of the electrolyte retention layer.

According to a seventh aspect of the present invention, there is provided the polymer actuator according to third aspect, wherein the electrolyte retention layer is a gel type substance.

According to such configuration, the polymer actuator can be obtained in which a sealing configuration and the like are not necessary and the volume availability efficiency is further enhanced compared to when the electrolyte retention layer is liquid.

According to an eighth aspect of the present invention, there is provided the polymer actuator according to the first aspect, wherein the first terminal member and the movable body contact by way of a second elastic body.

According to such configuration, the first terminal member comes under the influence of the forced displacement in the extending direction of the actuator through the second elastic body, and thus the external force applied to the polymer with the forced displacement in the extending direction can be reduced. A polymer actuator can thereby be obtained that suppresses lowering of performance when forced displacement is externally applied to the actuator with respect to the forced displacement in the extending direction.

According to a ninth aspect of the present invention, there is provided the polymer actuator according to the eighth aspect, wherein the second elastic body positioned between the first terminal member and the movable body is freely separable from the movable body.

According to such configuration, the polymer actuator can be obtained that can suppress lowering of performance even if forced displacement is applied in either the extending direction or the contracting direction of the actuator since the movable body and the second elastic body on the first terminal member side separate when forced displacement is applied to the actuator in the contracting direction.

According to a 10th aspect of the present invention, there is provided the polymer actuator according to the eighth or ninth aspect, wherein a rigidity of the first elastic body connecting the second terminal member and the movable body is smaller than a rigidity of the second elastic body arranged between the first terminal member and the movable body.

According to such configuration, the polymer actuator can be obtained that clarifies the role of applying a minimum pre-load in the extending direction of the polymer of the first elastic body connecting the second terminal member and the movable body and the role of performing minimum displacement that allows regulation of the displacement of the second elastic body arranged between the first terminal member and the movable body, and that can exhibit the effects more significantly.

According to an 11th aspect of the present invention, there is provided the polymer actuator according to the first aspect, wherein the first terminal member and the second terminal member are connected by way of the movable body, and the first terminal member and the second terminal member are directly connected by way of a third elastic body.

According to such configuration, the first terminal member is held even if forced displacement in the contracting direction is applied to the actuator and the movable body and the first terminal member separate, and the polymer is not likely to bend by the weight of the first terminal member and the like. Therefore, the polymer actuator that further can suppress lowering of performance can be obtained.

According to a 12th aspect of the present invention, there is provided the polymer actuator according to the first aspect, further comprising a protective mechanism for regulating a force acting between the first terminal member and the movable body to less than or equal to a constant value.

According to such configuration, the polymer actuator can be obtained that can suppress lowering of performance when forced displacement is externally applied to the actuator without suppressing the performance of the actuator since the external force applied to the polymer when forced displacement in the extending direction is applied to the actuator can be regulated without relying on the elasticity between the first terminal member and the movable body.

According to a 13th aspect of the present invention, there is provided the polymer actuator according to the eighth or ninth aspect, further comprising a protective mechanism for regulating a force acting between the first terminal member and the movable body to less than or equal to a constant value, the protective mechanism being a mechanism for regulating a deformation amount of the second elastic body arranged between the first terminal member and the movable body to less than or equal to a constant value.

According to such configuration, the polymer actuator can be obtained in which the regulation of the external force applied to the polymer when forced displacement in the extending direction is applied to the actuator can be achieved by limiting the displacement, whereby lowering of performance when forced displacement is externally applied to the actuator can be more easily suppressed.

According to a 14th aspect of the present invention, there is provided the polymer actuator according to the 13th aspect, further comprising a link mechanism for connecting the first terminal member and the movable body, wherein the protective mechanism is a mechanism for regulating a deformation of the link mechanism connecting the first terminal member and the movable body.

According to such configuration, the polymer actuator can be obtained in which the external force applied to the polymer when forced displacement in the extending direction is applied to the actuator can be easily regulated, whereby lowering of performance when forced displacement is externally applied to the actuator can be suppressed with a simple configuration.

According to a 15th aspect of the present invention, there is provided the polymer actuator according to the 12th aspect, wherein a force acting between the first terminal member and the movable body allowed by the protective mechanism changes according to a distance between the movable body and the second terminal member.

According to such configuration, the polymer actuator can be obtained in which the acceptable external force can be changed according to the extended or contracted amount of the polymer actuator, whereby limitation on the performance is further reduced while suppressing lowering of performance.

According to a 16th aspect of the present invention, there is provided the polymer actuator according to the first aspect, further comprising a control device for controlling the electrical stimulation to be applied to the actuator according to a distance between the movable body and the second terminal member.

According to such configuration, the polymer actuator excelling in positioning precision can be obtained since the displacement amount of the polymer actuator can be accurately adjusted by the control device.

According to a 17th aspect of the present invention, there is provided a robot arm driven by the polymer actuator according to the first or second aspect.

According to such configuration, the robot arm driven by the polymer actuator described in any one of the first to the 16th aspects can be configured, which robot arm can exhibit the effects of the polymer actuator.

According to an 18th aspect of the present invention, there is provided a robot comprising the robot arm according to the 17th aspect.

According to such configuration, the robot having the robot arm driven by the polymer actuator described in the 17th aspect can be configured, which robot can exhibit the effects of the polymer actuator.

Various embodiments of the present invention will now be described in detail based on the drawings.

First Embodiment

Figure 1B:
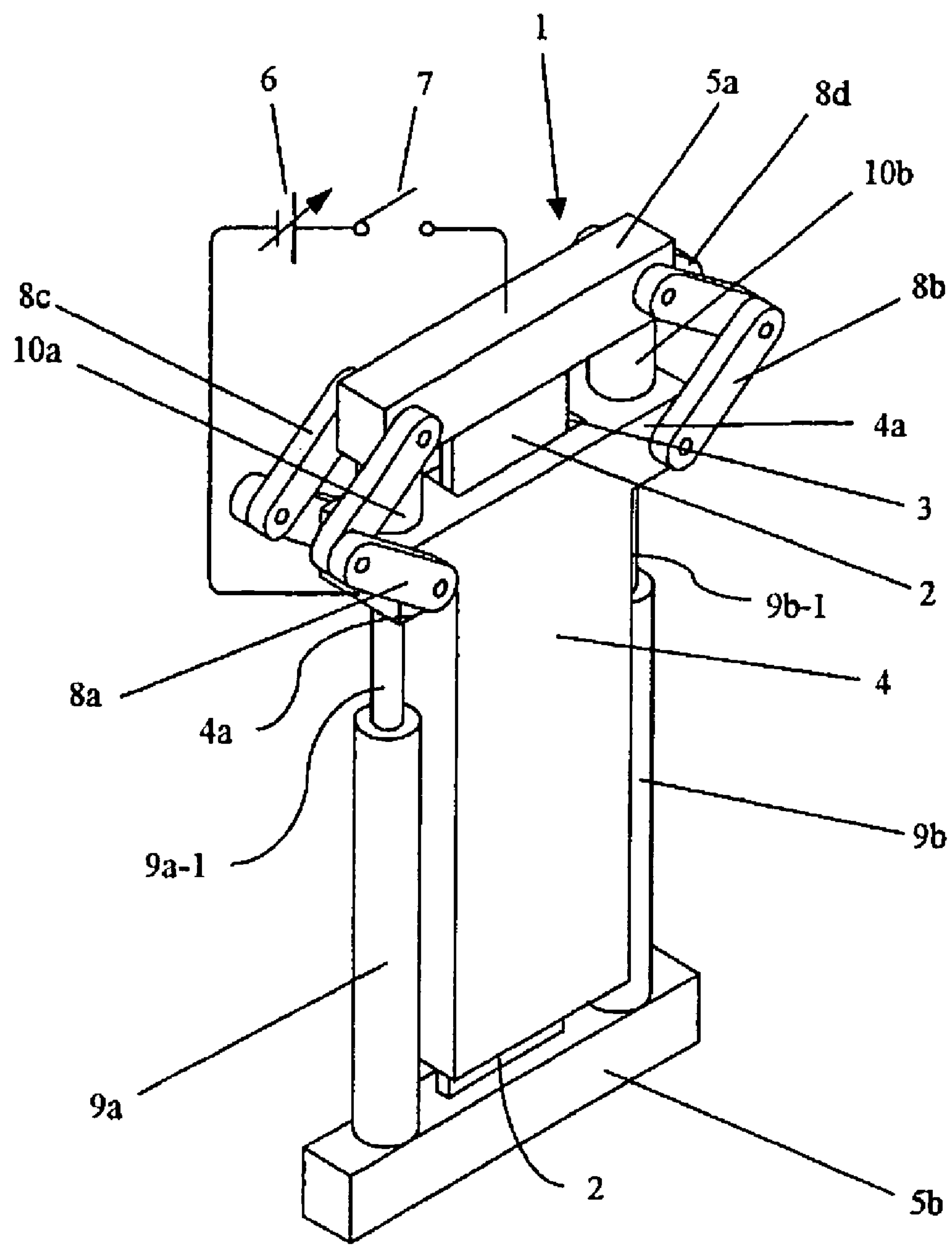
FIG. 1B is a schematic perspective view showing the artificial muscle actuator according to the first embodiment of the present invention.

FIGS. 1A and 1B are schematic perspective views showing an artificial muscle actuator 1 serving as one example of the polymer actuator according to a first embodiment of the present invention. FIG. 1B and FIGS. 2A to 2C show perspective views showing states in which sealing members 11*a*, 11*b* are entirely or partially removed.

Figure 9:
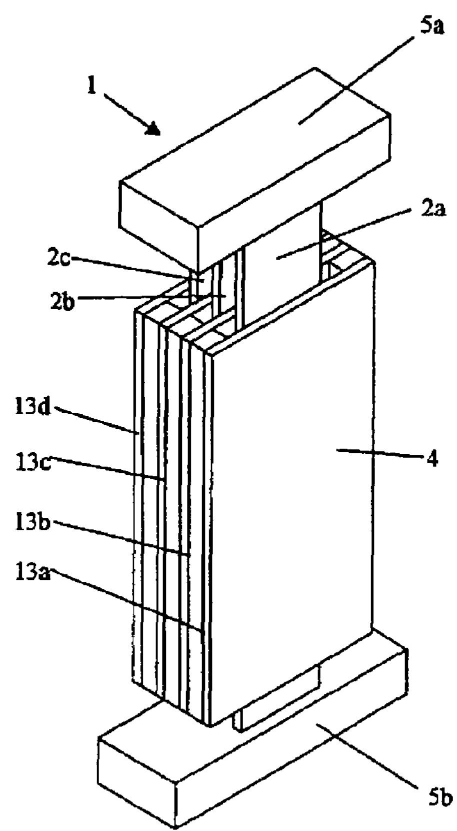
FIG. 9 is a schematic perspective view showing when using a plurality of polymer film members in the artificial muscle actuator according to the first embodiment of the present invention.

In FIGS. 1A and 1B, reference numeral 4 is a tubular movable body including electrodes and having a side surface of a T-shape, and the movable body 4 is connected to an extensible plate 2, which is an organic conductive polymer, serving as one example of the polymer film member having conductivity by way of a liquid electrolyte 3 serving as one example of the electrolyte retention layer. The extensible plate 2, which is the organic conductive polymer, is a film-shaped extensible plate arranged through the movable body 4 and having a quadrilateral or rectangular extensible body, and expanding or contracting deforms with oxidation reduction reaction by applying a potential difference between itself and the electrodes in the movable body 4. Polypyrrole, polyaniline, polymethoxyaniline, or the like can be used as the organic conductive polymer constituting the extensible plate 2, which is the organic conductive polymer, but polypyrrole is desirable in that the displacement is large. The thickness of the extensible plate 2 of the organic conductive polymer is desirably about a few dozen μm. The strength becomes weaker if thinner, and the ions cannot sufficiently move into or out of the extensible plate 2 of the organic conductive polymer if thicker. Various electrolytes such as aqueous solution, organic solvent, or ionic liquid may be used for the liquid electrolyte 3, but ionic liquid is desirable in that it has non-volatile properties. Furthermore, the electrode(s) to be applied with a potential difference between itself and the extensible plate 2 which is the organic conductive polymer, does not necessarily need to be included in the movable body 4, but the movable body and the electrode(s) are desirably integrated so that a space for the electrode(s) does not need to be prepared apart from the space occupied by the movable body 4. In particular, if the artificial muscle actuator 1 is configured by extensible plates 2*a* to 2*c* which are a plurality of organic conductive polymers, and a. plurality of electrodes 13*a* to 13*d* as shown in FIG. 9, the effect of enhancing the space availability efficiency can be improved with a configuration in which the movable body 4 includes the electrodes 13*a* to 13*d*. The components not necessary for the description are omitted in FIG. 9.

First and second terminal members (movable side terminal member and fixed side terminal member) 5*a*, 5*b* of a rectangular parallelepiped shape fixed so as to integrally operate with the extensible plate 2 which is the organic conductive polymer, are respectively connected to both ends of the extensible plate 2 which is the organic conductive polymer. The second terminal member 5*b* and the movable body 4 are connected with spring-embedded pistons 9*a*, 9*b*, serving as one example of the first elastic body. That is, the upper ends of piston rods 9*a*-1, 9*b*-1 of the spring-embedded pistons 9*a*, 9*b* erected and arranged in the vicinity of both ends of the second terminal member 5*b* are respectively connected to protruding parts 4*a* at the upper part of the movable body 4. The spring-embedded pistons 9*a*, 9*b* generate the driving forces in the extending direction of the piston rods 9*a*-1, 9*b*-1 by the springs embedded in the pistons 9*a*, 9*b*, and push the movable body 4 against columnar rubber members 10*a*, 10*b* serving as one example of the second elastic body. The rubber members 10*a*, 10*b* are arranged between the protruding parts 4*a* at the upper part of the movable body 4 and the vicinity of both ends of the first terminal member 5*a*, preferably coaxially with the piston rods 9*a*-1, 9*b*-1 of the spring-embedded pistons 9*a*, 9*b*. The natural lengths in a non-load state of the spring-embedded pistons 9*a*, 9*b* are constantly made long so that the movable body 4 can be pushed against the rubber members 10*a*, 10*b*. The rubber members 10*a*, 10*b* are fixed to the first terminal member 5*a* but are not fixed to the movable body 4, and thus can freely separate therefrom when the movable body 4 moves in an opposite direction from the rubber members 10*a*, 10*b*.

The first elastic body connecting the second terminal member 5*b* and the movable body 4 is not limited to spring-embedded pistons 9*a*, 9*b*, and may be of any type as long as similar functions are exhibited, for example, a flexible configuration simple body such as a coil spring, a combination thereof, or the like. Similarly, the second elastic body positioned between the first terminal member 5*a* and the movable body 4 is not limited to rubber members 10*a*, 10*b* and may be of any type as long as similar functions are exhibited. The rigidity of the first elastic body connecting the second terminal member 5*b* and the movable body 4 only needs to be an extent of producing the minimum driving force required when extending the actuator, whereas the rigidity of the second elastic body positioned between the first terminal member 5*a* and the movable body 4 does not need to be less than or equal to the rigidity that allows displacement to the extent that the external force in the pulling direction to be hereafter described can be regulated, and thus the rigidity of the first elastic body connecting the second terminal member 5*b* and the movable body 4 is desirably lower than the rigidity of the second elastic body positioned between the first terminal member 5*a* and the movable body 4.

The movable body 4 and the first and second terminal members 5*a*, 5*b* are respectively connected with tubular sealing members 11*a*, 11*b* for preventing the liquid electrolyte 3 from leaking out. Each of the sealing members 11*a*, 11*b* is desirably made of a flexible material that is not affected by the electrolytic solution of the liquid electrolyte 3 and that does not inhibit the movement of the movable body 4, and may be polyethylene, or a resin material such as fluorocarbon rein.

The front and back surfaces on both ends of the first terminal member 5*a* and the front and back surfaces of the protruding parts 4*a* at the upper part of the movable body 4 are coupled with link mechanisms 8*a* to 8*d* which couple two link plates into a “V” shape so as to oscillate with respect to each other, which link mechanisms 8*a* to 8*d* deform all together according to the distance between the first terminal member 5*a* and the movable body 4. A substantially U-shaped stopper member 12 (not shown in FIGS. 1A and 1B, see FIGS. 4A to 4C) serving as one example of the protective mechanism for restricting the deformation of the link mechanisms 8*a* to 8*d* is arranged on the external side of the link mechanisms 8*a* to 8*d*.

One of the wiring from the power supply 6 and the switch 7 is connected to the extensible plate 2 which is the organic conductive polymer, by way of the first terminal member 5*a*, and the other wiring is connected to the electrode(s) included in the movable body 4, so that the extensible plate 2 which is the organic conductive polymer, extends and contracts by electrical stimulation generated at a time when a potential difference supplied from the power supply 6 is applied between the extensible plate 2 which is the organic conductive polymer, and the electrode(s) included in the movable body 4.

The operation of the artificial muscle actuator 1 will now be described.

Figure 2A:
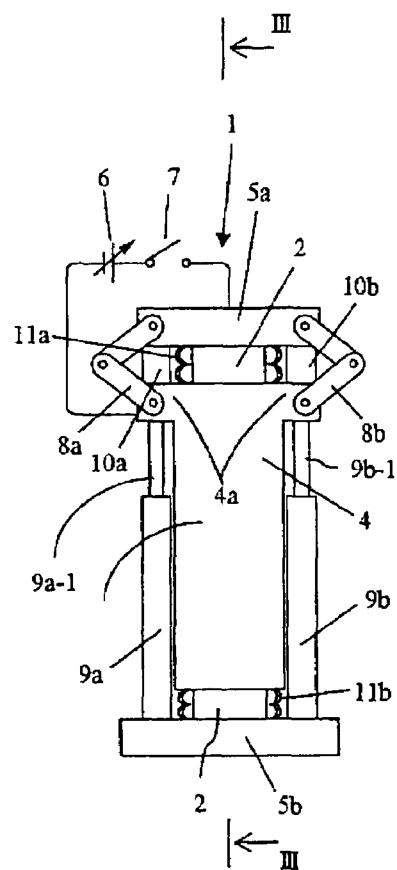
FIG. 2A is a front view showing the operation of the artificial muscle actuator according to the first embodiment of the present invention.
Figure 2B:
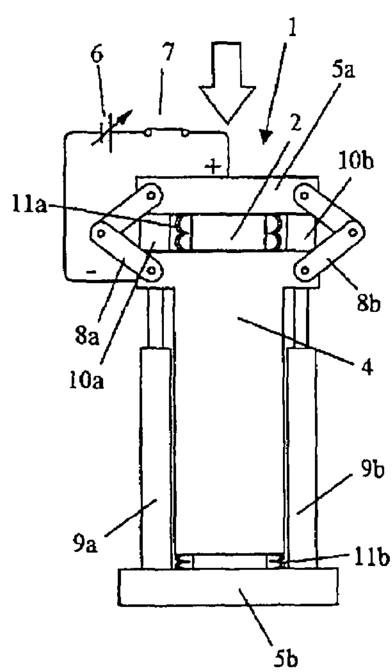
FIG. 2B is a front view showing the operation of the artificial muscle actuator according to the first embodiment of the present invention.
Figure 2C:
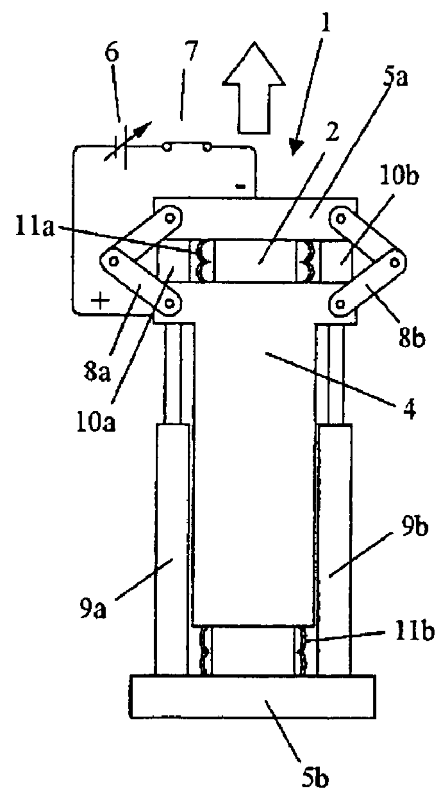
FIG. 2C is a front view showing the operation of the artificial muscle actuator according to the first embodiment of the present invention.
Figure 3A:
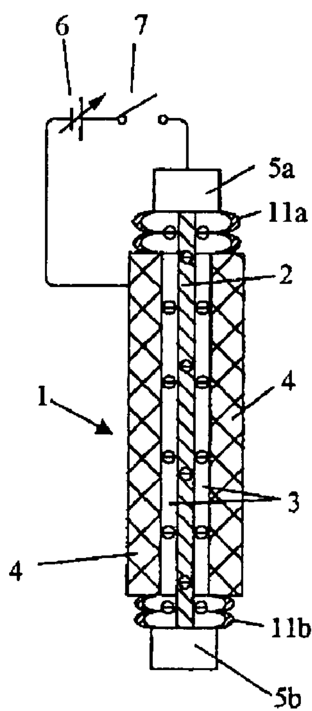
FIG. 3A is a side view showing the operation of the artificial muscle actuator according to the first embodiment of the present invention.
Figure 3B:
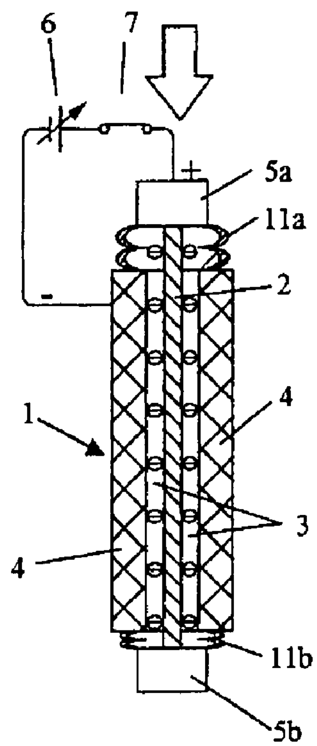
FIG. 3B is a side view showing the operation of the artificial muscle actuator according to the first embodiment of the present invention.
Figure 3C:
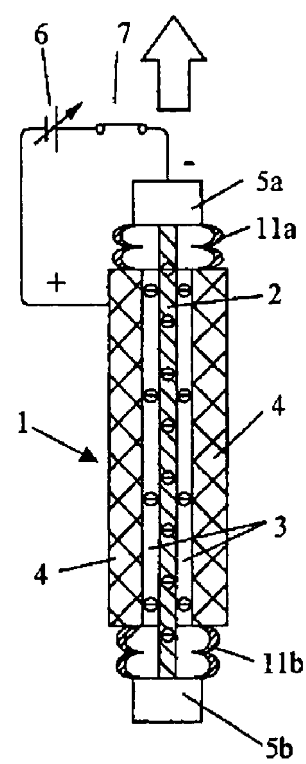
FIG. 3C is a side view showing the operation of the artificial muscle actuator according to the first embodiment of the present invention.

The cause of contraction of the extensible plate 2 of the conductive polymer includes coming and going (moving-in and -out-of) of anions (negative ions), coming and going of cations (positive ions), change in the polymer structure, or the like, but the coming and going of anions will be described in describing the principle of operation with FIGS. 3A, 3B, and 3C as doping and un-doping of anions are the main mechanism of deformation in the material system such polypyrrole. FIGS. 2A, 2B, and 2C are front views showing the change in state of the artificial muscle actuator 1 when the extensible plate 2 of the conductive polymer contracts, and FIGS. 3A, 3B, and 3C are cross sectional views viewed from the side showing the change in state of the artificial muscle actuator 1 when the extensible plate 2 of the conductive polymer contracts. Each cross sectional view is taken at the center of the front view of the artificial muscle actuator 1, for example, FIG. 3A is a cut cross sectional view taken along line III-III of FIG. 2A.

FIGS. 2A and 3A show a state in which the potential difference is not created between the extensible plate 2 of the conductive polymer and the electrode(s) included in the movable body 4 with the switch in the OFF state, and FIGS. 2B and 3B show a state in which a positive potential is applied to the extensible plate 2 of the conductive polymer and a negative potential is applied to the electrode(s) included in the movable body 4. FIGS. 2C and 3C show a state in which a negative potential is applied to the extensible plate 2 of the conductive polymer and a positive potential is applied to the electrode(s) included in the movable body 4. As shown in FIGS. 3A, 3B, and 3C, the extensible plate 2 of the conductive polymer extends when the anions enter inside, and contracts when the anions are discharged from the inside.

When the extensible plate 2 of the conductive polymer extends and contracts, the first terminal member 5*a* and the rubber members 10*a*, 10*b* move in conjunction therewith, and the movable body 4 pushed against the rubber members 10*a*, 10*b* by the spring-embedded pistons 9*a*, 9*b* also move in conjunction therewith. At this time, the rigidity of the rubber members 10*a*, 10*b* is higher than the rigidity of the spring-embedded pistons 9*a*, 9*b*, and the movement is performed with the distance between the first terminal member 5*a* and the movable body 4 barely changed. Simultaneously, the link mechanisms 8*a* to 8*d* also barely deform.

Figure 4A:
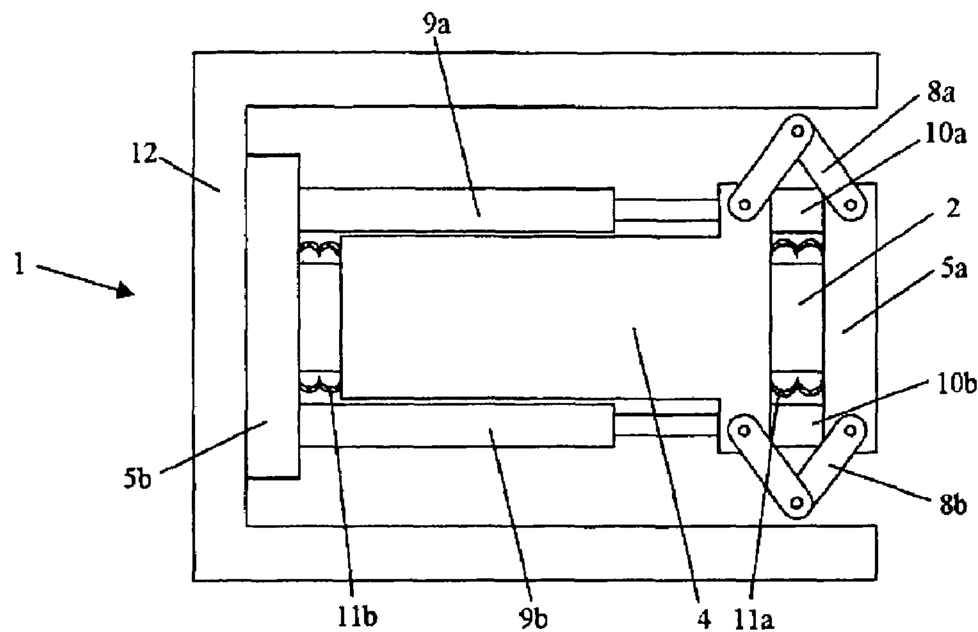
FIG. 4A is a front view showing the operation when forced displacement is applied from the outside of the artificial muscle actuator according to the first embodiment of the present invention.
Figure 4B:
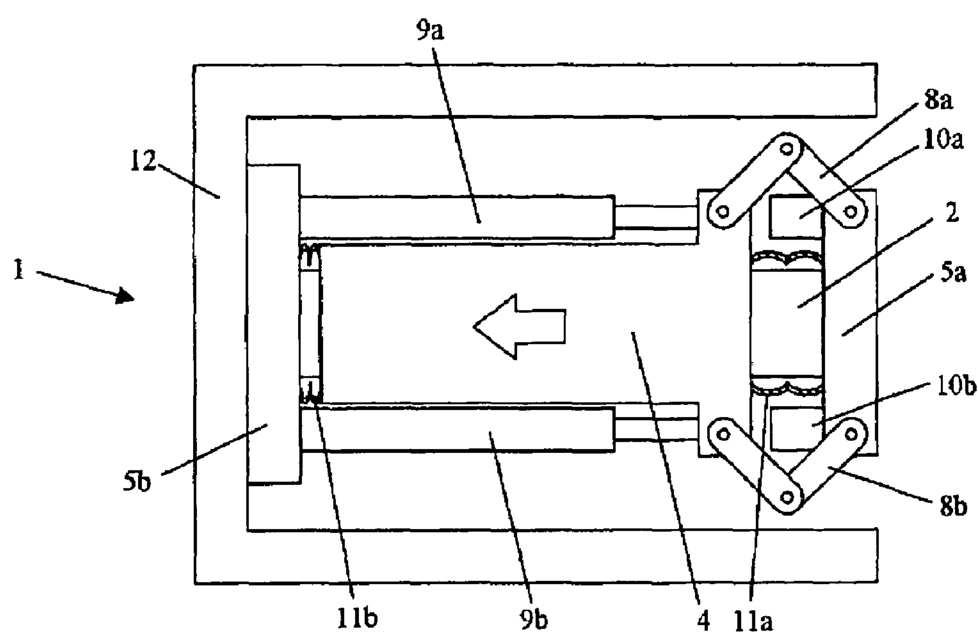
FIG. 4B is a front view showing the operation when forced displacement is applied from the outside of the artificial muscle actuator according to the first embodiment of the present invention.
Figure 4C:
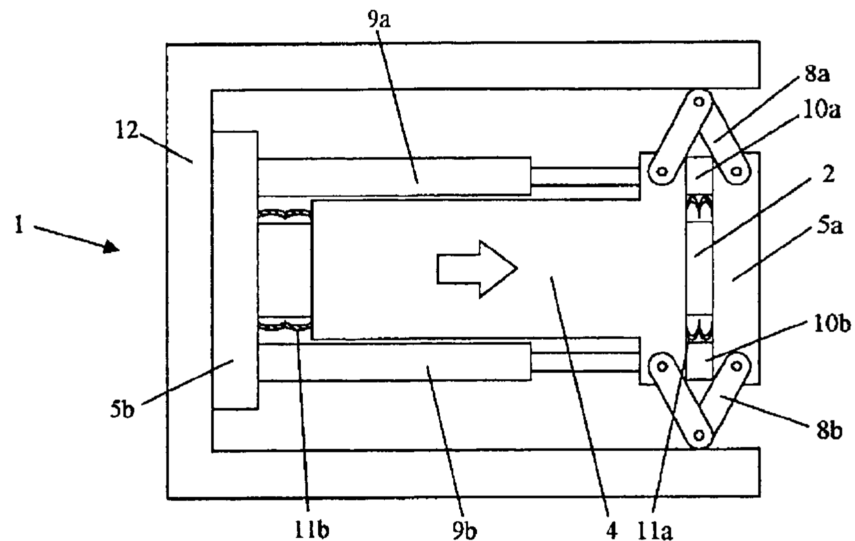
FIG. 4C is a front view showing the operation when forced displacement is applied from the outside of the artificial muscle actuator according to the first embodiment of the present invention.
Figure 5A:
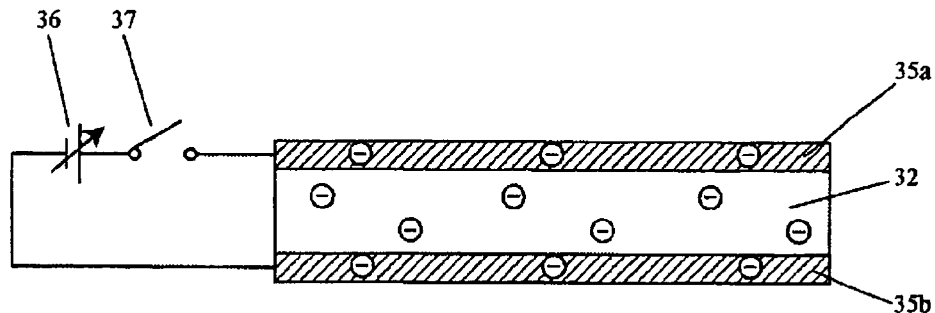
FIG. 5A is a schematic view showing an artificial muscle actuator of a conventional configuration.
Figure 5B:
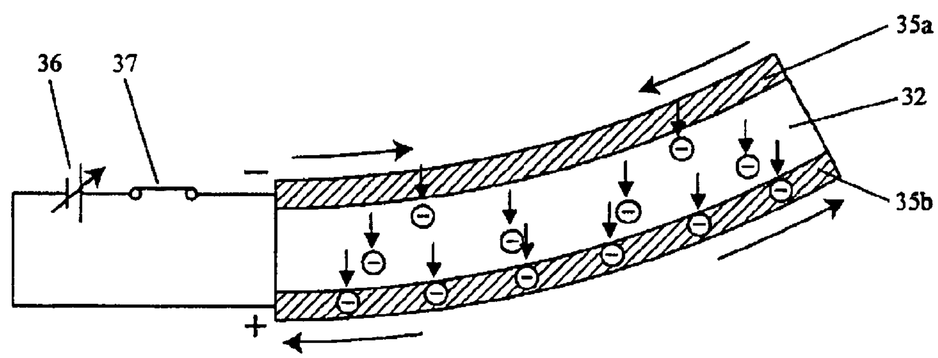
FIG. 5B is a schematic view showing the artificial muscle actuator of the conventional configuration.
Figure 5C:
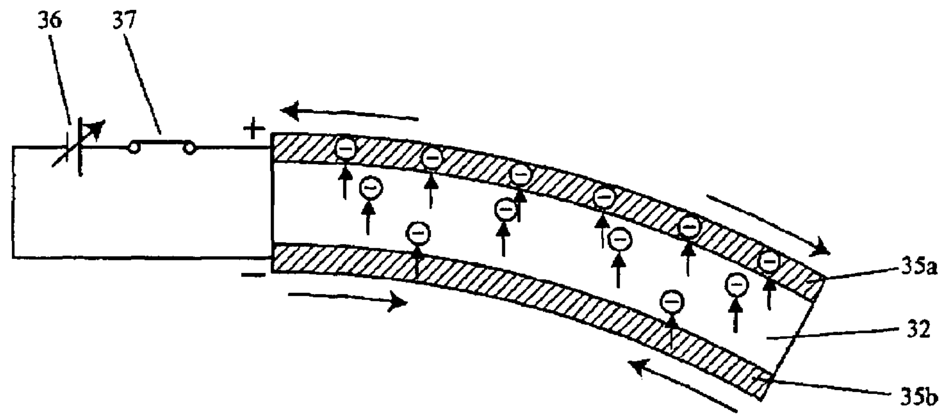
FIG. 5C is a schematic view showing the artificial muscle actuator of the conventional configuration.
Figure 6A:
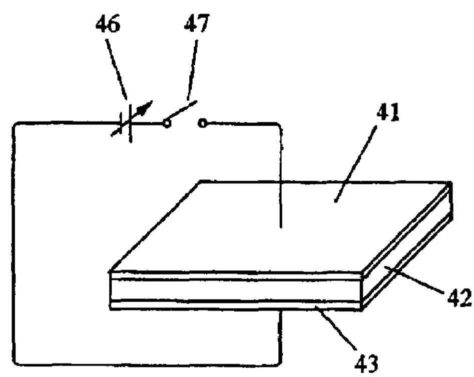
FIG. 6A is a schematic view showing the artificial muscle actuator of a conventional configuration different from FIG. 5A.
Figure 6B:
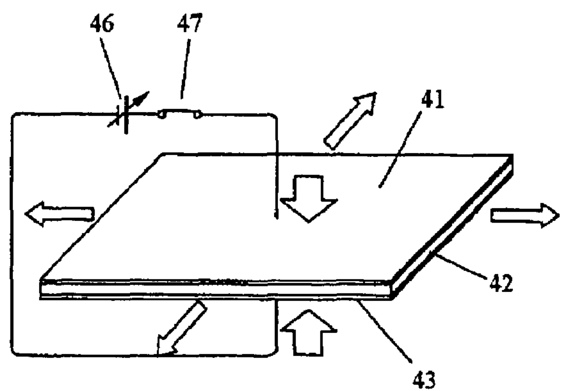
FIG. 6B is a schematic view showing the artificial muscle actuator of a conventional configuration different from FIG. 5A.
Figure 7:
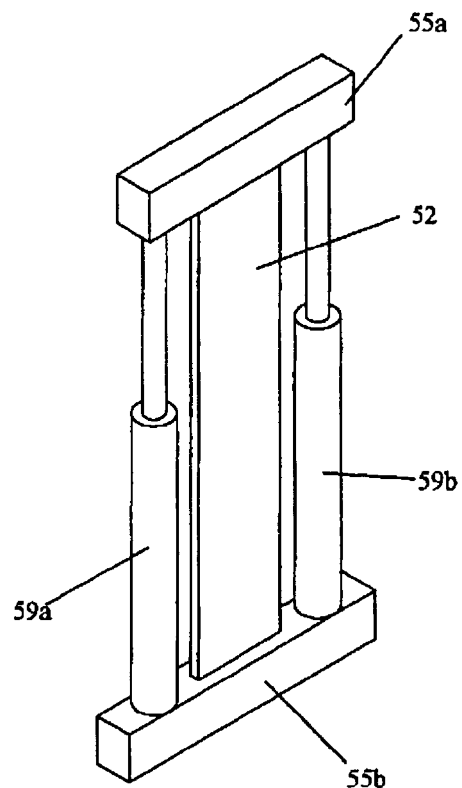
FIG. 7 is a perspective view showing a configuration of the artificial muscle actuator of the conventional configuration.
Figure 8A:
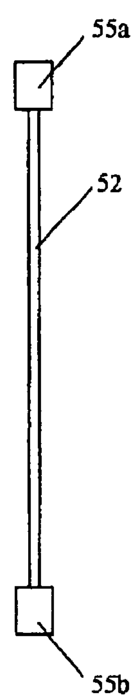
FIG. 8A is a side view showing the issue of the artificial muscle actuator of the conventional configuration.
Figure 8B:
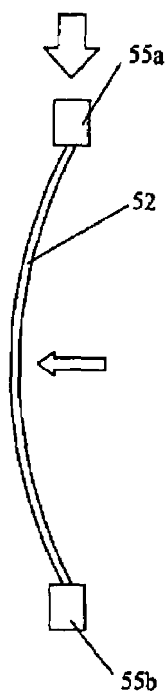
FIG. 8B is a side view showing the issue of the artificial muscle actuator of the conventional configuration.
Figure 11:
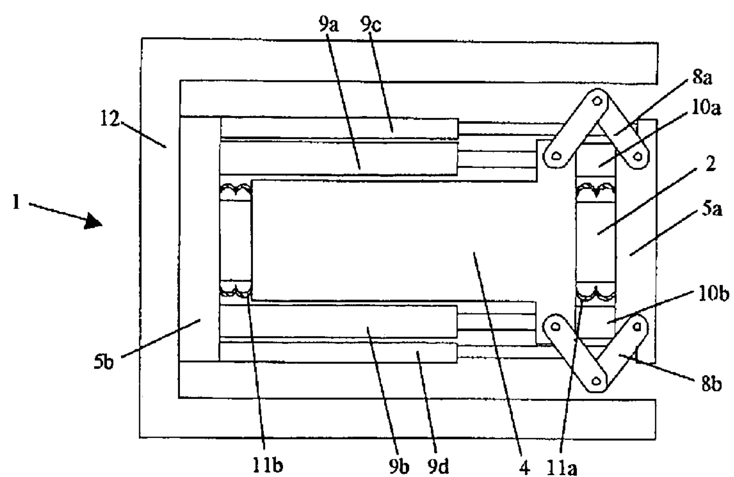
FIG. 11 is a front view of when a third elastic body is added in the artificial muscle actuator according to the first embodiment of the present invention.

A case when forced displacement is applied from the outside of the artificial muscle actuator 1 will now be described using FIGS. 4A, 4B, and 4C. FIG. 4A shows a state in which the forced displacement from the outside is not applied, FIG. 4B shows a state in which the forced displacement is applied in the contracting direction as shown with an arrow, and FIG. 4C shows a state in which the forced displacement is applied in the extending direction as shown with an arrow. In the state of FIG. 4B, the movable body 4 moves in the contracting direction according to the forced displacement. In this case, the movable body 4 is not pressed by the rubber members 10*a*, 10*b*, and thus the first terminal member 5*a* and the movable body 4 are connected only by way of the link mechanisms 8*a* to 8*d*. Since the link mechanisms 8*a* to 8*d* are freely deformable, the external force is not transmitted to the first terminal member 5*a* even if the movable body 4 is moved by forced displacement. The extensible plate 2 of the conductive polymer is also not affected by forced displacement and thus bending or the like will not occur. However, in this case as well, the extensible plate 2 of the conductive polymer may slightly bend due to the weight of the first terminal member 5*a* or the like depending on the direction of the gravitational force since the movable body 4 does not contact the rubber members 10*a*, 10*b*, and thus the first and second terminal members 5*a*, 5*b* are desirably directly connected using the spring-embedded pistons 9*c*, 9*d* serving as one example of the third elastic body, as shown in FIG. 11. According to the above configuration, the extensible plate 2 of the conductive polymer is therefore in a constantly stretched state and will not bend. The third elastic body is not limited to spring-embedded pistons 9*c*, 9*d* and may be of any type as long as similar functions are exhibited, for example, a flexible configuration simple body such as a coil spring, a combination thereof, or the like.

In the state of FIG. 4C, the movable body 4 moves in the extending direction according to the forced displacement. In this case, the movable body 4 is pressed against the rubber members 10*a*, 10*b*, and the rubber members 10*a*, 10*b* are compressed by the amount of external force. The distance between the first terminal member 5*a* and the movable body 4 accordingly becomes closer, and the link mechanisms 8*a* to 8*d* deform. When the compressed amount of the rubber members 10*a*, 10*b* corresponding to the external force reaches a constant value, the bent portion of the link of each link mechanism 8*a* to 8*d* contacts the stopper member 12, whereby further external force cannot be transmitted to the first terminal member 5*a* (in other words, the force acting between the first terminal member 5*a* and the movable body 4 can be regulated to be smaller than or equal to a constant value). In other words, the deformation amount of the rubber members 10*a*, 10*b* serving as one example of the second elastic body arranged between the first terminal member 5*a* and the movable body 4 can be regulated to be smaller than or equal to the constant value. Therefore, even if the forced displacement is applied to the movable body 4, the external force applied to the extensible plate 2 of the conductive polymer is limited to smaller than or equal to the constant value, thereby preventing irreversible deformation of the extensible plate 2 of the conductive polymer by forced displacement. The deformation amount of the link mechanisms 8*a* to 8*d* regulated by the stopper member 12 do not all need to be constant, and may be changed according to the length of the extensible plate 2 of the conductive polymer. For example, such adjustment that the more the extensible plate 2 of the conductive polymer becomes in the extending state, the more the allowable deformation amount or the like reduces can be considered. Such adjustment can be easily achieved by having the distance between the surfaces of the stopper member 12 contacted by the link mechanisms 8*a* to 8*d* gradually narrow from the left side to the right side in any one of the figures of FIGS. 4A to 4C.

The liquid electrolyte 3 serving as one example of the electrolyte retention layer is used in the first embodiment, but such electrolyte retention layer does not necessarily need to be liquid, and may be a gel electrolyte. The gel electrolyte is desirable because it eliminates the necessity of sealing configuration such as covers 11*a*, 11*b*. Furthermore, the polymers having conductivity also do not need to be an organic conductive polymer, and may be a gel or solid polymer body containing a carbon material such as carbon nanotubes, or carbon nano particles, or a substance having conductivity such as metal particles. Similar effects can still be obtained with such configuration. Moreover, such materials are desirable in that the conductivity and the property serving as the configuration body can be independently adjusted easily.

In addition, the dielectric polymer having electrodes on both surfaces may be used in place of the polymer having conductivity. In this case, similar effects can be obtained by connecting the power supply 6 and the switch 7 between the electrodes arranged on both surfaces of the dielectric polymer. FIGS. 2B and 4B correspond to the state in which the switch is turned OFF, FIGS. 2C and 4C correspond to the state in which the switch is turned ON, and the influence of the polarity of the power supply is eliminated. The present invention encompasses both cases.

Figure 10:
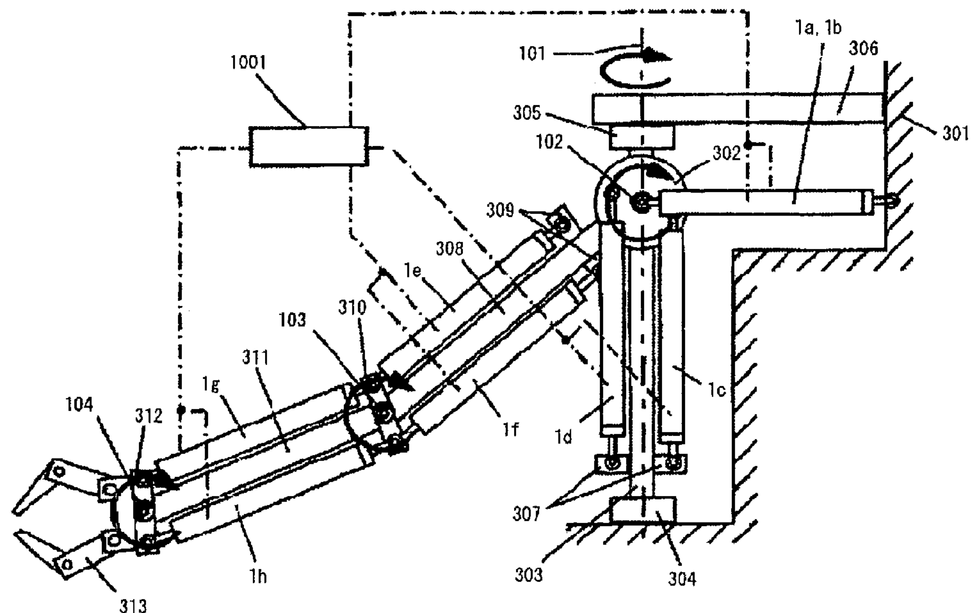
FIG. 10 is a schematic view of the robot arm using the artificial muscle actuator according to the first embodiment of the present invention.

A configuration example of the robot arm using a plurality of artificial muscle actuators 1 according to the first embodiment is shown in FIG. 10. A pair of driving sections of each robot arm is configured as antagonist muscle configuration by a set of two artificial muscle actuators among artificial muscle actuators 1*a* to 1*h* each having a configuration similar to the artificial muscle actuator 1. One driving section of the pair of driving sections of each robot arm is extended and the other driving section is contracted, or vice versa, so that a forward and reverse rotational movement is possible at shafts 101 to 104 coupled with the pair of driving sections of the robot arm. Specifically, in the configuration of FIG. 10, the vertical shaft 101 forward and reverse rotates by the extending and contracting operations of the artificial muscle actuators 1*a*, 1*b*, and similarly, the shaft 102 by the extending and contracting operations of the artificial muscle actuators 1*c*, 1*d*, the shaft 103 by the extending and contracting operations of the artificial muscle actuators 1*e*, 1*f*, and the shaft 104 by the extending and contracting operations of the artificial muscle actuators 1*g*, 1*h*, forward and reverse rotate respectively.

More specifically, the robot arm with four degrees of freedom is configured by a first joint vertical shaft 101 that forward and reverse rotates in plane in the lateral direction along the vertical direction axis, a second joint shaft 102 that forward and reverse rotates in plane along the vertical direction, a third joint shaft 103 that mutually forward and reverse rotates between a second arm 308 and a first arm 311, and a fourth joint shaft 104 that mutually forward and reverse rotates between the first arm 311 and a hand 313 with respect to a fixed wall 301.

At the first joint 101, circular supporting bodies 302, 302 are coupled in a freely rotating manner at both sides of the upper end of a rotating shaft 303 having its upper and lower ends supported at bearings 304 and 305 in a freely rotating manner along the vertical direction. One ends of the artificial muscle actuators 1*a*, 1*b* (artificial muscle actuator 1*b* is not shown as it is arranged behind the artificial muscle actuator 1*a*) are coupled to the fixed wall 301, and the other ends are coupled to the supporting shaft 102 (second joint shaft 102) of each circular supporting body 302. Therefore, the first arm 311, the second arm 308, and the hand 313 of the robot arm can be integrally forward and reverse rotationally moved in plane along the lateral direction about the first joint vertical shaft 101 by the antagonist drive of the artificial muscle actuators 1*a*, 1*b*. The bearing 305 on the upper side is fixed at the fixed wall 301 by way of a supporting rod 36.

At the second joint, one end of the second arm link 308 is fixed at two circular supporting bodies 302, 302 fixed on both sides of the rotating shaft 303. The artificial muscle actuators 1*c*, 1*d* are coupled between the circular supporting bodies 302, 302 of the second arm link 308 and supporting bodies 307, 307 fixed at one end of the rotating shaft 303 so as to be orthogonal thereto, whereby the first arm 311, the second arm 308, and the hand 313 of the robot arm integrally forward and reverse rotate in plane along the vertical direction about the lateral axis or the second joint supporting shaft 102 by the antagonist drive of the artificial muscle actuators 1*c*, 1*d*.

At the third joint, the artificial muscle actuators 1*e*, 1*f* are coupled between a supporting body 310 coupled in a freely rotating manner along the second arm 308 and intersecting the second arm 308 at the distal end of the second arm 308 and having the basal end of the first arm 311 fixed thereto, and supporting bodies 309, 309 fixed to the basal end of the second arm 308 so as to be orthogonal thereto, whereby the first arm 311 and the hand 313 integrally forward and reverse rotate in plane along the vertical direction about the lateral axis or the third joint supporting shaft 103 by the antagonist drive of the artificial muscle actuators 1*e*, 1*f*.

At the fourth joint, the artificial muscle actuators 1*g*, 1*h* are coupled between the supporting body 310 intersecting the first arm 311 and fixed to the basal end of the first arm 311 along the first arm 311 between the distal end of the second arm 308 and the basal end of the first arm 311, and a supporting body 312 intersecting the first arm 311 and fixed at the basal end of the hand 313 between the distal end of the first arm 311 and the basal end of the hand 313, whereby the hand 313 forward and reverse rotates in plane along the vertical direction about the lateral axis or the third joint supporting shaft 103 by the antagonist drive of the artificial muscle actuators 1*g*, 1*h*.

With regards to each artificial muscle actuators 1*a*, 1*b*; the artificial muscle actuators 1*c*, 1*d*; the artificial muscle actuators 1*e*, 1*f*; and the artificial muscle actuators 1*g*, 1*h*, the voltage of the power supply 6 and the state of the switch 7 are appropriately controlled according to the respective distance between the respective movable body 4 and the second terminal member 5*b* by a control computer 1001 serving as one example of the control device, so that the contracting and extending operations of each of the artificial muscle actuators 1*a*, 1*b*; the artificial muscle actuators 1*c*, 1*d*; the artificial muscle actuators 1*e*, 1*f*; and the artificial muscle actuators 1*g*, 1*h* are controlled.

According to such configuration, the robot arm having multi-degree of freedoms and enabling flexible movement as with the arms of humans can be obtained. The robot arm particularly suited for household applications can be thus achieved.

By properly combining the arbitrary embodiments of the aforementioned various embodiments, the effects possessed by the embodiments can be produced.

The polymer actuator according to the present invention provides the polymer actuator that can suppress lowering of performance when the forced displacement is externally applied to the actuator without suppressing the performance of the actuator, and is effective as an artificial muscle actuator and the like. Therefore, the robot arm using the polymer actuator as a driving device and the robot equipped with the robot arm are also effective.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A polymer actuator being driven by extension and contraction of a polymer by electrical stimulation; the polymer actuator comprising:

a polymer film member configured by the polymer;

a first terminal member connected to one end of the polymer film member;

a second terminal member connected to the other end of the polymer film member; and a movable body connected to the second terminal member by way of a first elastic body and capable of being pressed against a first terminal member side; wherein a displacement generated by extension and contraction of the polymer film member is taken out by way of the movable body connected to the second terminal member which is connected to the other end of the polymer film member, by way of the first elastic body and pressed against the first terminal member which is connected to the one end of the polymer film member, by an elastic force of the first elastic body.

2. The polymer actuator according to claim 1, wherein the polymer actuator includes two electrodes and the polymer film member of a dielectric polymer arranged therebetween, and is driven by extension and contraction generated at the dielectric polymer by applying a potential difference between the electrodes.

3. The polymer actuator according to claim 1, wherein the polymer actuator includes the polymer film member of the polymer having conductivity, and an electrode connected to the polymer having the conductivity by way of an electrolyte retention layer, and is driven by extension and contraction generated at the polymer having the conductivity by applying a potential difference between the polymer having the conductivity and the electrode.

4. The polymer actuator according to claim 3, wherein the movable body includes the polymer film member of the polymer having the conductivity and the electrode connected to the polymer film member by way of the electrolyte retention layer.

5. The polymer actuator according to claim 3, wherein the polymer having the conductivity is a polymer comprising an organic conductive polymer.

6. The polymer actuator according to claim 3, wherein the polymer having the conductivity comprises a carbon material having conductivity.

7. The polymer actuator according to claim 3, wherein the electrolyte retention layer is a gel type substance.

8. The polymer actuator according to claim 1, wherein the first terminal member and the movable body contact by way of a second elastic body.

9. The polymer actuator according to claim 8, wherein the second elastic body positioned between the first terminal member and the movable body is freely separable from the movable body.

10. The polymer actuator according to claim 8, wherein a rigidity of the first elastic body connecting the second terminal member and the movable body is smaller than a rigidity of the second elastic body arranged between the first terminal member and the movable body.

11. The polymer actuator according to claim 1, wherein the first terminal member and the second terminal member are connected by way of the movable body, and the first terminal member and the second terminal member are directly connected by way of a third elastic body.

12. The polymer actuator according to claim 1, further comprising a protective mechanism for regulating a force acting between the first terminal member and the movable body to less than or equal to a constant value.

13. The polymer actuator according to claim 8, further comprising a protective mechanism for regulating a force acting between the first terminal member and the movable body to less than or equal to a constant value, the protective mechanism being a mechanism for regulating a deformation amount of the second elastic body arranged between the first terminal member and the movable body to less than or equal to a constant value.

14. The polymer actuator according to claim 13, further comprising a link mechanism for connecting the first terminal member and the movable body, wherein the protective mechanism is a mechanism for regulating a deformation of the link mechanism connecting the first terminal member and the movable body.

15. The polymer actuator according to claim 12, wherein a force acting between the first terminal member and the movable body allowed by the protective mechanism changes according to a distance between the movable body and the second terminal member.

16. The polymer actuator according to claim 1, further comprising a control device for controlling the electrical stimulation to be applied to the actuator according to a distance between the movable body and the second terminal member.

17. A robot arm driven by the polymer actuator according to claim 1.

18. A robot comprising the robot arm according to claim 17.

* * * * *